United States Patent [19]
Sriwongjanya et al.

[11] Patent Number: 6,156,342
[45] Date of Patent: *Dec. 5, 2000

[54] CONTROLLED RELEASE ORAL DOSAGE FORM

[75] Inventors: Mongkol Sriwongjanya, Davie; Timothy Weng, Plantation; Joseph Chou, Coral Springs; Chih-Ming Chen, Davie, all of Fla.

[73] Assignee: Andex Pharmaceuticals, Inc., Fort Lauderdale, Fla.

[ * ] Notice: This patent issued on a continued prosecution application filed under 37 CFR 1.53(d), and is subject to the twenty year patent term provisions of 35 U.S.C. 154(a)(2).

[21] Appl. No.: 09/084,622

[22] Filed: May 26, 1998

[51] Int. Cl.[7] .................. A61K 9/24; A61K 9/28
[52] U.S. Cl. .............. 424/473; 424/464; 424/474; 424/489
[58] Field of Search ................... 424/473, 464, 424/474, 489

[56] References Cited

U.S. PATENT DOCUMENTS

| | | |
|---|---|---|
| 5,073,379 | 12/1991 | Klimesch et al. . |
| 5,223,541 | 6/1993 | Maryanoff et al. . |
| 5,336,691 | 8/1994 | Raffa et al. . |
| 5,395,626 | 3/1995 | Kotwal et al. . |
| 5,468,744 | 11/1995 | Raffa et al. . |
| 5,474,786 | 12/1995 | Kotwal et al. . |
| 5,516,803 | 5/1996 | Raffa . |
| 5,580,578 | 12/1996 | Oshlack et al. . |
| 5,591,452 | 1/1997 | Miller et al. . |
| 5,601,842 | 2/1997 | Bartholomaeus . |
| 5,639,476 | 6/1997 | Oshlack et al. . |
| 5,645,858 | 7/1997 | Kotwal et al. . |

FOREIGN PATENT DOCUMENTS

| | | |
|---|---|---|
| 0147780 | 12/1984 | European Pat. Off. . |
| WO8504249 | 2/1998 | WIPO . |

OTHER PUBLICATIONS

50TH Edition of Physcan's Desk Reference, pp. 1585–1587 @ 1996.

*Primary Examiner*—Thurman K. Page
*Assistant Examiner*—Lakshmi Channavajjala
*Attorney, Agent, or Firm*—Hedman, Gibson & Costigan, P.C.

[57] ABSTRACT

A controlled release dosage form for an analgesic that does not contain an expanding polymer and comprising a core containing the analgesic, preferably tramadol or it pharmaceutically acceptable deviates and a semipermeable membrane coating the core.

19 Claims, 5 Drawing Sheets

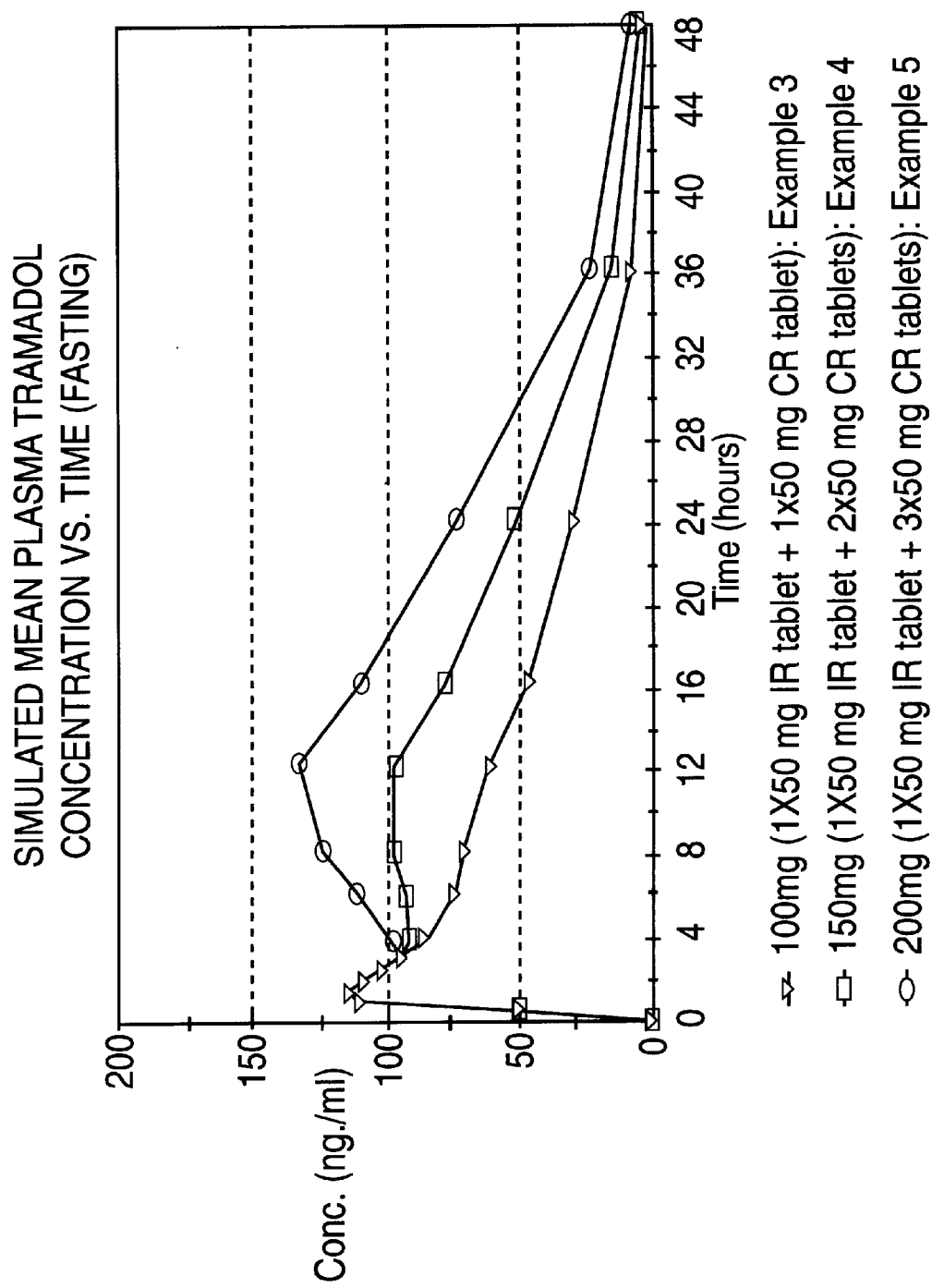

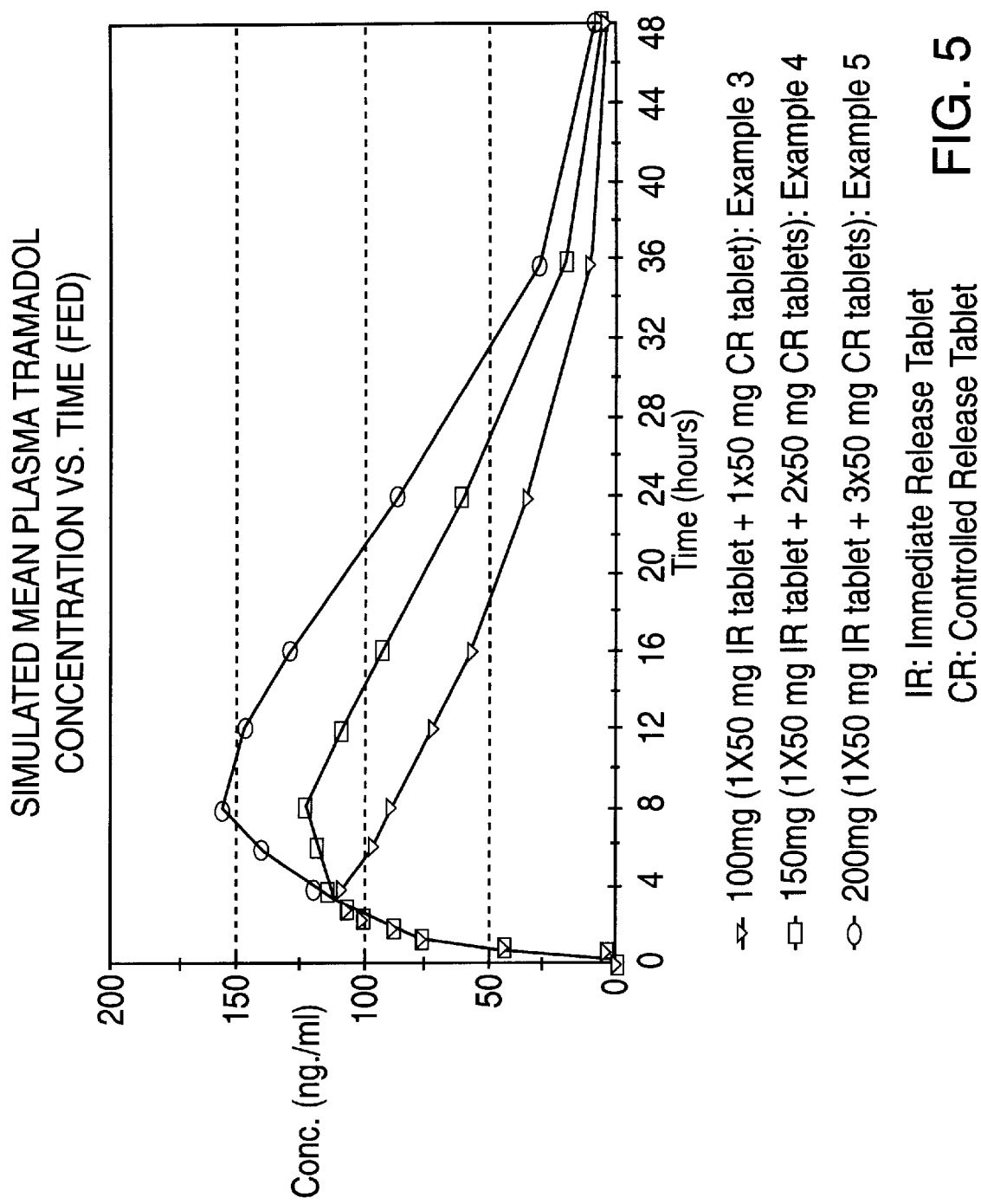

CONTROLLED RELEASE ORAL DOSAGE FORM

BACKGROUND OF THE INVENTION

The present invention relates to oral controlled release dosage formulations containing an analgesic. More specifically, the present invention relates to an oral dosage formulation in the form of a capsule, tablet or pellet comprising a water soluble analgesic such as tramadol or its pharmaceutically acceptable derivatives which are described in U.S. Pat. Nos. 5,516,803, 5,336,691 and 5,468,7442 and are incorporated herein by reference.

In the prior art are extended release tablets which have an osmotically active drug core surrounded by a semipermeable membrane. These tablets function by allowing a fluid such as gastric or intestinal fluid to permeate the coating membrane and dissolve the active ingredient so it can be released through a passageway in the membrane. If the active ingredient is insoluble in the permeating fluid, a hydrogel is employed to push the active ingredient through the passageway. Some representative examples of these osmotic tablet systems can be found in U.S. Pat. Nos. 3,845,770, 3,916,899, 3,952,741, 4,034,758, 4,077,407 and 4,783,337.

The basic osmotic device described in the above-cited patents has been refined over time in an effort to provide greater control of the release of the active ingredient. For example U.S. Pat. Nos. 4,777,049 and 4,851,229 describe an osmotic dosage form comprising a semipermeable wall surrounding a core. The core contains an active ingredient and a modulating agent wherein the modulating agent causes the active ingredient to be released through a passageway in the semipermeable membrane in a pulsed manner. Further refinements are described in U.S. Pat. Nos. 5,178,867, 4,587,117 and 4,522,625 which include modifications to the semipermeable membrane surrounding the active core or as described in U.S. Pat. Nos. 5,650,170 and 4,892,739 which include increasing the number of coatings surrounding the active core.

Also in the prior art are techniques for preparing controlled release formulations that comprise encapsulating a plurality of beads or pellets coated with a diffusion barrier such as U.S. Pat. Nos. 5,376,384, 5,529,790, 5,470,584, 5,002,776, 5,445,829, 5,578,321, 4,524,060, 4,752,470. These patents teach obtaining a controlled release of an active ingredient by varying the coating level of the diffusion barriers and/or the composition of the diffusion barriers. These patents also teach the combination of beads with varying release profiles to obtain a desired composite release profile.

None of the above described prior art references suggest a controlled release formulation that employs the drug tramadol or its pharmaceutically acceptable derivatives as the active ingredient. Further none of the above-cited patents suggest an osmotic tablet or pellet with a unitary core that does not contain a binding agent or an expanding agent.

Tramadol, (1R, 2R or 1S, 2S)-2-[(dimethylamino)methyl]-1-(3-methoxyphenyl)-cyclohexanol, is a class of analgesic cycloalkanol-substituted phenol esters having a basic amine group in the cycloalkyl ring which is described in greater detail in U.S. Pat. No. 3,652,589 and incorporated herein by reference. Tramadol is believed to produce an analgesic effect through a mechanism that is neither fully opioid-like nor non-opioid-like because clinical data suggests that tramadol lacks many of the typical side effects of opioid antagonists such as respiratory depression, constipation, tolerance and abuse liability but can produce hot flashes and sweating. Due to combination of non-opioid and opioid activity, tramadol is a very unique analgesic and many attempts have been made to prepare oral formulations of the drug. For example an immediate release oral formulation of tramadol is commercially available from McNeil Pharmaceuticals under the tradename ULTRAM®.

The 50th Edition of the Physician's Desk Reference, copyright 1996, p. 1585, states that peak plasma levels for the ULTRAM® product occur about two (2) hours after dosing but this time can vary slightly depending upon the racemic mixture of tramadol employed in the dosage form. Other attempts at preparing useful dosage forms of tramadol have been directed to combining tramadol with other drugs such as non-steroidal anti-inflammatory drugs, acetaminophen or codeine as described in U.S. Pat. Nos. 5,516,803, 5,468,744 and 5,336,691.

Attempts have also been made to formulate tramadol into controlled release formulations such as those described in: U.S. Pat. Nos. 5,395,626, 5474,786 and 5,645,858 which employ a plurality of coating layers to control the release of tramadol over time; U.S. Pat. Nos. 5,580,587 and 5,639,476 which employ a coating of an aqueous dispersion of hydrophobic acrylic polymers dried for an extended period of time under rigid conditions; U.S. Pat. Nos. 5,601,842 and 5,591,452 which employ a polymer matrix to control the release of the drug; and European Patent Application No. 147 780 which employs a super hydrolyzed polyvinyl alcohol coating that gels in the aqueous environment of the body and controls the release of the drug. These controlled release formulations for tramadol are very labor intensive to prepare.

It is an object of the present invention to provide a controlled or sustained release dosage formulation for an analgesic that is easy to manufacture and can be used to prepare a range of dosing levels.

It is a further object of the present invention to provide a controlled or sustained release dosage formulation for an analgesic that does not obtain peak plasma levels for at least four (4) hours, preferably six to twenty hours and most preferably ten to eighteen hours, after administration.

It is also a further object of the present invention to provide a controlled or sustained release dosage formulation for an analgesic that does not employ an expanding polymer or a binding agent.

It is also a further object of the present invention to provide a controlled or sustained release dosage formulation for an analgesic that can be prepared with only one or two coating layers.

It is an additional object of the present invention to provide a controlled or sustained release dosage formulation for an analgesic that can provide continuous and non-pulsating therapeutic levels of the analgesic to an animal or human in need of such treatment over a twelve hour to twenty-four hour period.

It is also an object of this invention to provide a controlled or sustained release pharmaceutical tablet or pellet having only a homogeneous osmotic core wherein the osmotic core component may be made using ordinary tablet compression techniques.

It is also an object of this invention to provide a controlled or sustained release pharmaceutical formulation comprising an immediate release tablet or pellet and a controlled release tablet or pellet.

SUMMARY OF THE INVENTION

The foregoing objectives are met by a controlled release dosage form comprising:

(a) a core comprising an analgesic;

(b) a semipermeable membrane coating surrounding the core; and (c) a means for releasing the analgesic from the core.

The means for releasing the analgesic from the core can be a passageway that is drilled, punched or formed into the semipermeable membrane or it may be a channel, preferably a tortuous channel, formed in the semipermeable membrane by the erosion of a water soluble channeling agent. The channeling agent is incorporated into the semipermeable membrane during processing of the dosage form and erodes or leaches from the semipermeable membrane after administration of the dosage form to the environment of use.

The controlled release dosage form can be manufactured in the form of a tablet or pellet and can incorporate an immediate release form of the analgesic. If the controlled release dosage form is a tablet, it is preferred that the immediate release amount of the analgesic be coated onto the semipermeable membrane or be a separate tablet. If the controlled release dosage form is a pellet, it is preferred that the immediate release amount of the analgesic be a pellet.

In a preferred embodiment, the core comprises an analgesic, a diluent, a flow aid and a lubricant and the coating comprises an insoluble polymer, a plasticizer and a mixture of channeling agents comprising a channeling agent that is soluble under stomach and intestinal conditions and a channeling agent that is insoluble under stomach conditions but is soluble under intestinal conditions.

The dosage form of the present invention may also contain a water soluble seal coat between the core and the semipermeable membrane.

BRIEF DESCRIPTION OF THE DRAWINGS

FIG. 4 is a graph depicting the simulated in vivo tramadol plasma profile of the formulations described in Examples 3, 4 and 5 under fasting conditions.

FIG. 5 is a graph depicting the simulated in vivo tramadol plasma profile of the formulations described in Examples 3, 4 and 5 under fed conditions.

DETAILED DESCRIPTION OF THE INVENTION

Figure 1:
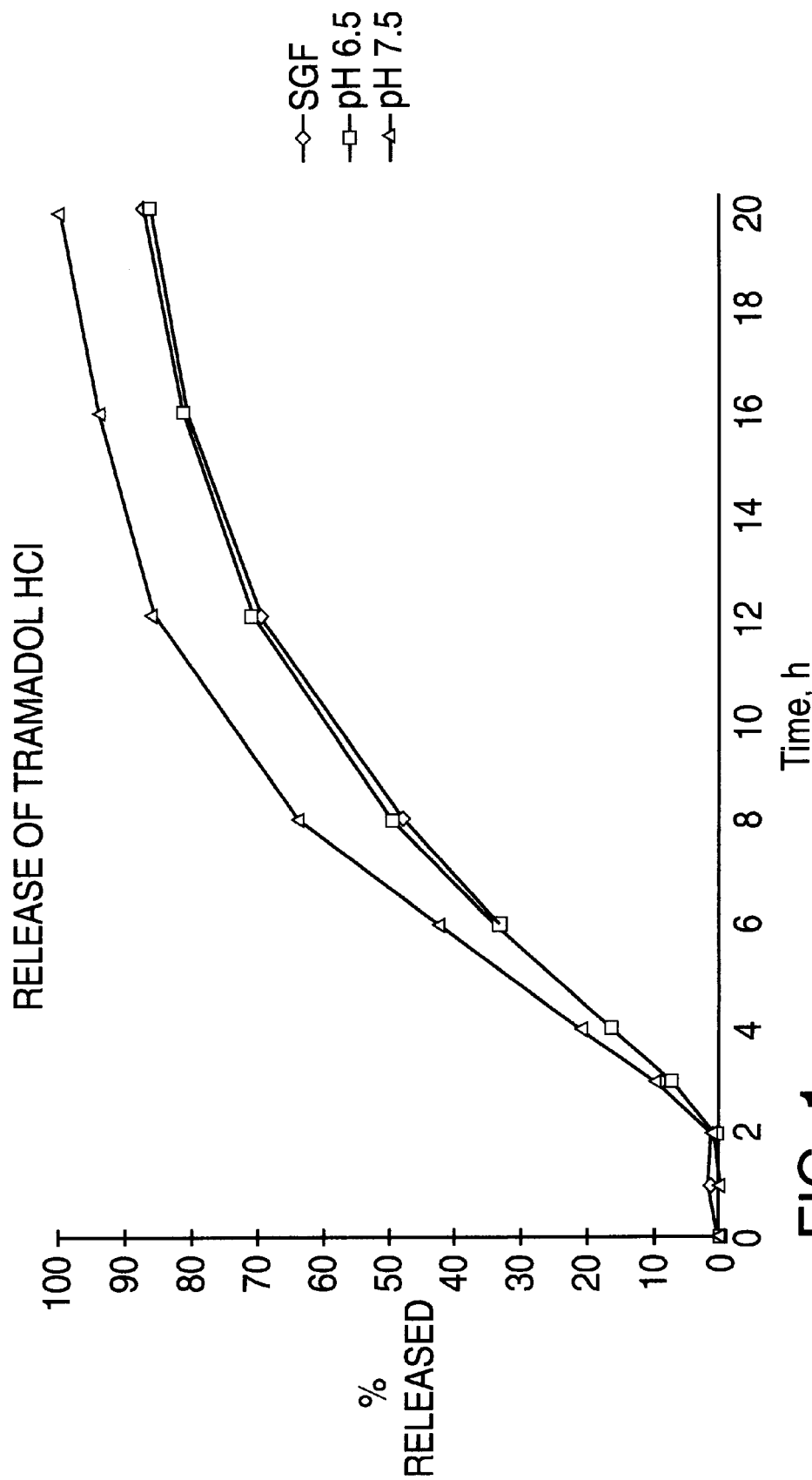
FIG. 1 is a graph which depicts the dissolution profile in simulated intestinal fluid (pH 7.5 phosphate buffer), simulated gastric fluid (SGF) and pH 6.5 of the formulation described in Example 2 as tested according to the procedure described in United States Pharmacopeia XXIII, Apparatus 1@100 rpm.

The phrase "controlled release dosage form" as used in this specification refers to a tablet or pellet that exhibits a controlled or sustained release of an active ingredient, such as tramadol, over an 8 to 12 hour time period and does not obtain a peak plasma level for about 3 to 4 hours, preferably about 6 to 20 hours and most preferably about 10 to 18 hours after administration.

The term analgesic as used in this specification refers to drugs that are useful in relieving or controlling pain without disturbing consciousness or altering other sensory modalities. The analgesic may be an opiate such a morphine or codeine or a nonopiate such as acetaminophen, aspirin, ibuprofen, or naproxen. Other analgesics are described in Remington's Pharmaceutical Sciences, 1995 Edition and are incorporated herein by reference. It is preferred that the analgesic used in the present invention be water soluble.

The preferred analgesic for use in the present invention is tramadol or its pharmaceutically acceptable derivatives. The pharmaceutically acceptable derivatives of tramadol include the N-oxide derivative such as described in U.S. Pat. No. 5,223,541, the O-desmethyl derivative, individual stereoismers, mixtures of stereoisomers, including racemates, pharmaceutically acceptable salts, such as the hydrochloride salt, solvates and polymorphs.

The core of the present invention comprises the analgesic and may optionally comprise other known excipients commonly known in the art. Some common excipients are binding agents such as polyvinyl pyrrolidone, diluents such as lactose monohydrate NF, flow agents such as colloidal silicon dioxide, lubricants such as magnesium stearate and absorption enhancers such as sodium lauryl sulfate. Preferably any excipient that is incorporated into the core should be water soluble.

In a preferred embodiment of the present invention the core will comprise the following ingredients:

| INGREDIENT | PREFERRED | MOST PREFERRED |
| --- | --- | --- |
| analgesic | 5–100% | 10–30% |
| diluent | 0–95% | 70–90% |
| flow aid | 0–2% | 0.1–1% |
| lubricant | 0–2% | 0.1–1% | all the percentages in the above table are based on the total weight of the core.

The core of the present invention, which comprises the analgesic, is prepared by dry granulating the core ingredients and compressing the granules into tablets or by direct compression. The core may also be formed by wet granulating methods and compressing the granules with the addition of a lubricant into a tablet on a rotary press.

Other commonly known excipients may also be included into the core such as pigments or dyes.

The homogeneous core is coated with a semipermeable membrane, preferably a modified polymeric membrane to form the controlled release tablet of the invention. The semipermeable membrane is permeable to the passage of an external fluid such as water and biological fluids and is impermeable to the passage of the analgesic in the core. Materials that are useful in forming the semipermeable membrane are cellulose esters, cellulose diesters, cellulose triesters, cellulose ethers, cellulose ester-ether, cellulose acylate, cellulose diacylate, cellulose triacylate, cellulose acetate, cellulose diacetate, cellulose triacetate, cellulose acetate propionate, and cellulose acetate butyrate. Other suitable polymers are described in U.S. Pat. Nos. 3,845,770, 3,916,899, 4,008,719, 4,036,228 and 4,11210, which are incorporated herein by reference. The most preferred semipermeable membrane material is cellulose acetate comprising an acetyl content of 39.3 to 40.3%, commercially available from Eastman Fine Chemicals.

In a preferred embodiment, the semipermeable membrane can be formed from the above-described polymers and (a) channeling agent(s).

The channeling agent increases the volume of fluid imbibed into the core and creates channels, preferably tortuous channels, to enable the dosage form to dispense the analgesic. The channeling agent can be a water soluble material or an enteric material. Some examples of the preferred materials that are useful as channeling agents are sodium chloride, potassium chloride, sucrose, sorbitol, mannitol, polyethylene glycol (PEG), propylene glycol, hydroxypropyl cellulose, hydroxypropyl methycellulose, hydroxypropyl methylcellulose phthalate, cellulose acetate phthalate, polyvinyl alcohols, methacrylic acid copolymers and mixtures thereof. The preferred channeling agents are PEG 400, confectioner's sugar and Eudragit S100, a methacrylic acid copolymer commercially available from Röhm Pharma Gmbh. The most preferred channeling agent is a mixture of soluble material such a confectioner's sugar and an enteric material such as Eudragit S100.

The channeling agent may also be a drug that is water soluble. If the channeling agent is a drug, such as tramadol, the present dosage form has the added advantage of providing an immediate release of the drug, which is selected as the channeling agent.

The channeling agent comprises approximately 0 to about 50% of the total weight of the coating, most preferably about 5% to about 40% of the total weight of the coating.

The semipermeable membrane may also be formed with commonly known excipients such a plasticizer. Some commonly known plasticizers include adipate, azelate, enzoate, citrate, stearate, isoebucate, sebacate, triethyl citrate, tri-n-butyl citrate, acetyl tri-n-butyl citrate, citric acid esters, and those described in the Encyclopedia of Polymer Science and Technology, Vol. 10 (1969), published by John Wiley & Sons. The preferred plasticizers are triacetin, acetylated monoglyceride, grape seed oil, olive oil, sesame oil, acetyltributylcitrate, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate, and the like. Depending on the particular plasticizer, amounts from about 0 to about 30%, and preferably about 3% to about 15% of the plasticizer can be used based upon the total weight of the coating.

As used herein the term passageway includes an aperture, orifice, bore, hole, weaken area or an erodible element such as a gelatin plug that erodes to form an osmotic passageway for the release of the analgesic from the dosage form. A detailed description of the passageway can be found in U.S. Pat. Nos. such as 3,845,770, 3,916,899, 4,034,758, 4,077,407, 4,783,337 and 5,071,607.

In a preferred embodiment the coating of the present invention will have the following composition:

| COATING: | Preferred | Most Preferred |
|---|---|---|
| semipermeable polymer | 50–100% | 40–80% |
| channeling agent | 0–50% | 5–40% |
| plasticizer | 0–30% | 3–15% |

The percentages listed in the above table are based on the total weight of the coating.

Generally, the coating around the core will comprise from about 1% to about 30% and preferably about 5% to about 25% based on the total weight of the core and coating.

In a preferred embodiment, the dosage form will comprises at least one controlled release tablet and optionally at least one immediate release tablet. The controlled release tablet will comprise a core and a semipermeable membrane as described above. The immediate release tablet comprises a core as described above and optionally a water soluble seal coat prepared from materials commonly known in the industry such as Opadry Clear.

The controlled release tablet(s) and the immediate release tablet(s) are placed in a hard gelatin capsule, preferably size "00" or "A" for administration to an animal or human in need of analgesic treatment.

By preparing the controlled release tablets and immediate release tablets with a standard amount of analgesic, such as 50 mg, a number of sustained released dosage forms can be prepared with varying amounts of analgesic. For example one (1) 50 mg immediate release tablet and one (1) 50 mg controlled release tablet may be combined in a hard gelatin capsule to provide a sustained release of 100 mg of analgesic to a patient over a twelve to twenty-four hour time period. Similarly, one (1) 50 mg immediate release tablet may be combined with two (2) 50 mg controlled released tablets in a hard gelatin capsule to provide a sustained release of 150 mg of analgesic to a patient over a twelve to twenty-four hour time period or one (1) 50 mg immediate release tablet may be combined with three (3) 50 mg controlled release tablets in a hard gelatin capsule to provide a sustained release of 200 mg of analgesic to a patient over a twelve to twenty-four hour time period. Alternatively, two (2) 50 mg controlled release tablets, three (3) 50 mg controlled release tablets or four (4) controlled release tablets may be filled in a hard gelatin capsule to provide a sustained release of 100, 150 or 200 mg of analgesic, respectively, to a patient over a twelve to twenty-four hour time period. The standard tablets allow the dosage form to be easily tailored to meet the individual and unique needs of a particular patient.

The controlled release dosage tablets or pellets, prepared according to the present invention should exhibit the following dissolution profile when tested in a USP type 1 apparatus at 100 rpms in 900 ml of simulated intestinal fluid (pH 7.5 phosphate buffer) and at 37° C.:

| Time (hours) | Preferred | Most Preferred |
|---|---|---|
| 2 | 0–20% | 0–10% |
| 4 | 5–40% | 10–35% |
| 8 | 30–75% | 40–70% |
| 12 | NLT 50% | NLT 60% |
| 16 | NLT 60% | NLT 70% |
| 20 | NLT 70% | NLT 80% |

NLT = NOT LESS THAN

The immediate release tablets or pellets prepared according to the present invention should exhibit the following dissolution profile when tested in a USP type 1 apparatus at 100 rpms in 900 ml of simulated intestinal fluid (pH 7.5 phosphate buffer) and at 37° C.:

| Time (hours) | Preferred | Most Preferred |
|---|---|---|
| 2 | 0–100% | 30–100% |
| 4 | NLT 50% | NLT 70% |

NLT = NOT LESS THAN

The sustained release dosage form of the present invention which comprises at least one controlled release tablet and at least one immediate release tablet should exhibit the following dissolution profile when tested in a USP type 1 apparatus at 100 rpms in 900 ml of simulated intestinal fluid (pH 7.5 phosphate buffer) and at 37° C.:

| Time (hours) | Preferred | Most Preferred |
| --- | --- | --- |
| 2 | 0–70% | 0–60% |
| 4 | 10–90% | 30–80% |
| 8 | 30–95% | 40–90% |
| 12 | NLT 50% | NLT 60% |
| 16 | NLT 60% | NLT 70% |
| 20 | NLT 70% | NLT 80% |

NLT = NOT LESS THAN

DESCRIPTION OF THE PREFERRED EMBODIMENTS

EXAMPLE 1

An immediate release tablet containing 50 mg of tramadol HCl and having the following formula is prepared as follows:

| I | IR TABLET |
| --- | --- |
| tramadol HCl | 16.67% |
| lactose monohydrate NF[1] | 82.33% |
| colloidal silicon dioxide | 0.5% |
| magnesium stearate | 0.5% |

[1]spray dried.

(a) Tabletting

The tramadol HCl, lactose, colloidal silicon dioxide and magnesium stearate are delumped by passing them through a 40 mesh screen. The delumped materials, tramadol HCl, lactose, and colloidal silicon dioxide, are then blended for approximately thirty (30) minutes in a suitable blender. The delumped magnesium stearate is then added to the blender and blended for five (5) minutes. After blending, the mixture is compressed on a rotary press with tooling that has an indentation.

(b) Seal Coating (optional)

The immediate release core tablet is seal coated with an Opadry material or other suitable water-soluble coating material. The seal coating is prepared by dissolving 30 g of Opadry Clear and 10 g of sodium chloride in 1000 g of purified water. The Opadry solution is then sprayed onto the core tablet using a pan coater under the following conditions: exhaust air temperature of 38–42° C.; atomization pressure of 28–40 psi; and spray rate of 10–15 ml/min. The core tablet is coated with the sealing solution until a theoretical coating level of approximately 3–4% is obtained.

EXAMPLE 2

A controlled release tablet containing 50 mg of tramadol HCl is prepared by first preparing an immediate release core as described in Example 1. The immediate release core is then coated with a controlled release coating. The controlled release tablet has the following formula:

| II | CR Tablet |
| --- | --- |
| immediate release core (seal coated)[2] | 87.50% |
| cellulose acetate (398-10)[3] | 7.50% |
| Eudragit S100 | 2.50% |
| triacetin | 0.625% |
| PEG 400 | 0.625% |
| sugar[4] | 1.250% |

[2]core from Example 1
[3]acetyl content 39.3–40.3%
[4]confectioner's 6X-micronized The cellulose acetate, Eudragit S100, triacetin and PEG 400 are dissolved in a mixture of acetone and isopropyl alcohol and stirred until a clear solution is obtained. The sugar is then dispersed in the polymer solution by a homogenizer. The coating suspension is then sprayed onto the seal coated core in a fluidized bed coater employing the following conditions: product temperature of 26–32° C.; atomization pressure of approximately 3 bars; and spray rate of 15–35 ml/min. The sealed core tablet is coated until a theoretical coating level of approximately 12.5% is obtained.

The resulting controlled release dosage form is tested in simulated intestinal fluid (pH 7.5), simulated gastric fluid (SGF) and pH 6.5 according to the procedure described in United States Pharmacopeia XXIII, Apparatus 1 @ 100 rpm and found to have the following release profile:

| TIME (hours) | SIF % Released | SGF % Released | pH 6.5 % Released |
| --- | --- | --- | --- |
| 2 | 1 | 1 | 0 |
| 4 | 21 | 16 | 16 |
| 8 | 63 | 47 | 49 |
| 12 | 85 | 69 | 70 |
| 16 | 93 | 80 | 80 |
| 20 | 99 | 86 | 85 |

The release profile in pH 7.5, SGF and pH 6.5 of the controlled release product prepared in this Example is shown in FIG. 1.

Figure 2:
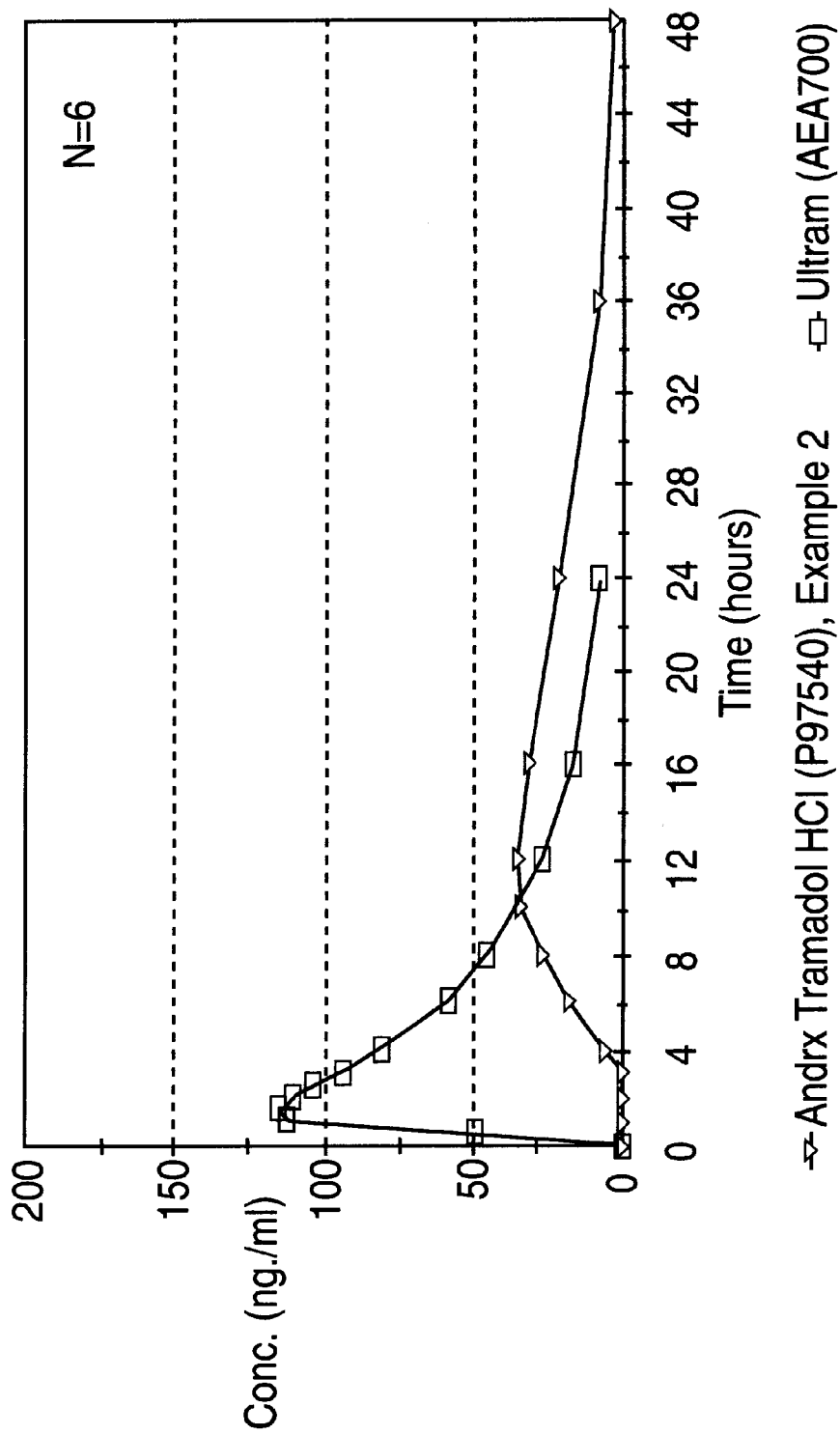
FIG. 2 is a graph depicting the in vivo tramadol plasma profile of the formulation described in Example 2 and the in vivo tramadol plasma profile of the commercially available tramadol product ULTRAM® under fasting conditions.

FIG. 2 depicts the in vivo tramadol plasma profile of the controlled release product prepared in this Example under fasting conditions. Also shown in FIG. 2 is the in vivo tramadol plasma profile of ULTRAM®, a commercially available pharmaceutical product containing the drug tramadol HCl.

Table 1 is a summary of the bioavailability comparison data, test/reference ratio, shown in FIG. 2 wherein the ULTRAM® product is the reference product in a two way crossover biostudy with n=6.

TABLE 1

| | Test Mean | % CV | Ref Mean | % CV | G-Mean Ratio |
| --- | --- | --- | --- | --- | --- |
| Cmax | 39.88 | 26.68 | 119/60 | 32.56 | 0.339 |
| AUC (O-t) | 800.67 | 51.59 | 904.63 | 66.03 | 0.942 |
| AUC (O-24/48) | 808.24 | 50.52 | 904.63 | 66.03 | 0.954 |
| Tmax | 11.33 | 24.11 | 1.58 | 41.97 | 7.544 |

Figure 3:
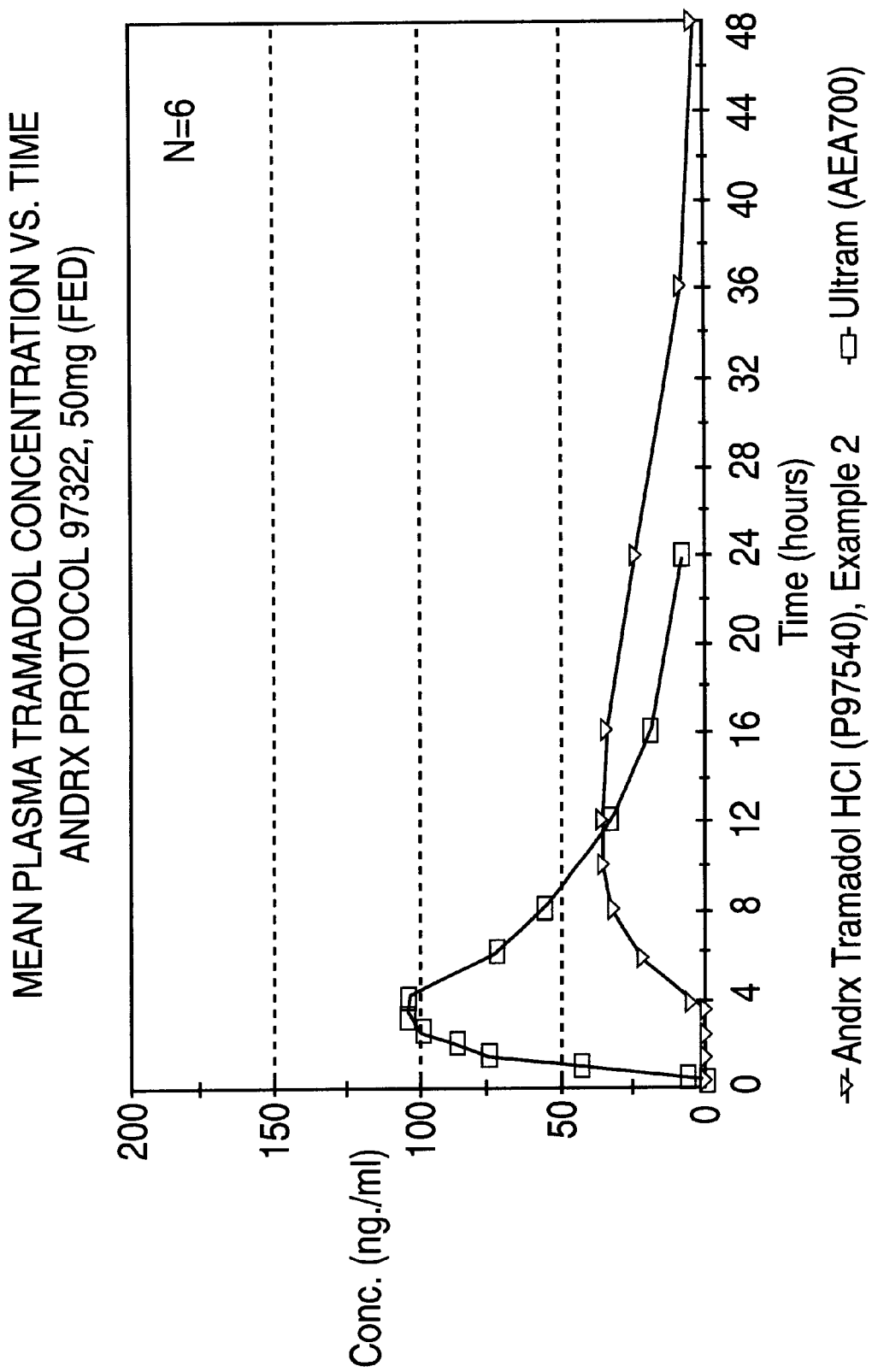
FIG. 3 is a graph depicting the in vivo tramadol plasma profile of the formulation described in Example 2 and the in vivo tramadol plasma profile of the commercially available tramadol product ULTRAM® under fed conditions.

FIG. 3 depicts the in vivo tramadol plasma profile of the sustained release product prepared in this Example under fed conditions. FIG. 3 also shows the in vivo tramadol plasma profile of the ULTRAM® product under fed conditions.

Table 2 is a summary of the bioavailability comparison data, test/reference ratio, shown in FIG. 3 wherein the ULTRAM® product is the reference product in a two way crossover biostudy with n=6.

TABLE 2

|  | Test Mean | % CV | Ref Mean | % CV | G-Mean Ratio | A-Mean Ratio |
|---|---|---|---|---|---|---|
| Cmax | 39.30 | 24.82 | 113.55 | 19.40 | 0.343 | 0.347 |
| AUC (O-t) | 902.31 | 34.72 | 1013.85 | 34.55 | 0.888 | 0.896 |
| AUC (O-24/48) | 902.31 | 34.72 | 1013.85 | 34.55 | 0.888 | 0.896 |
| Tmax | 10.33 | 28.49 | 3.17 | 29.40 | 3.295 | 3.450 |

EXAMPLE 3

A 100 mg once a day tramadol sustained release dosage form is prepared by placing one (1) immediate release tablet from Example 1 and one (1) controlled release tablet from Example 2 in a hard gelatin capsule commercially available from Capsugel.

FIG. 4 depicts the simulated in vivo tramadol plasma profile of the sustained release product prepared in this Example under fasting conditions.

FIG. 5 depicts the simulated in vivo tramadol plasma profile of the sustained release product prepared in this Example under fed conditions.

EXAMPLE 4

A 150 mg once a day tramadol sustained release dosage form is prepared by placing one (1) immediate release tablet from Example 1 and two (2) controlled release tablets from Example 2 in a hard gelatin capsule commercially available from Capsugel.

FIG. 4 depicts the simulated in vivo tramadol plasma profile of the sustained release product prepared in this Example under fasting conditions.

FIG. 5 depicts the simulated in vivo tramadol plasma profile of the sustained release product prepared in this Example under fed conditions.

EXAMPLE 5

A 200 mg once a day tramadol sustained release dosage form is prepared by placing one (1) immediate release tablet from Example 1 and three (3) controlled release tablets from Example 2 in a hard gelatin capsule commercially available from Capsugel.

FIG. 4 depicts the simulated in vivo tramadol plasma profile of the sustained release product prepared in this Example under fasting conditions.

FIG. 5 depicts the simulated in vivo tramadol plasma profile of the sustained release product prepared in this Example under fed conditions.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

We claim:

1. A sustained release capsule dosage form comprising
   a) at least one controlled release tablet or pellet consisting of:
      (i) a core consisting of:
         (1) 10–30% of a drug selected from the group consisting of tramadol or a pharmaceutically acceptable derivative of tramadol;
         (2) 70–90% of diluent;
         (3) 0.1–1% of a flow aid;
         (4) 0.1–1% of a lubricant;
      (ii) A semipermeable membrane coating covering said core wherein the semipermeable membrane consists of 40–80% of a water insoluble cellulose derivative; 3–15% of a plasticizer; and 5–40% of a means for releasing the drug from the core; and
   b) at least one immediate release tablet or pellet comprising:
      (1) a core comprising:
         (1) 5–100% of a drug selected from the group consisting of tramadol or a pharmaceutically acceptable derivative of tramadol;
         (2) 0–95% of a diluent;
         (3) 0–2% a flow aid;
         (4) 0–2% a lubricant; and
         (5) optionally a seal coat around the core.

2. A sustained release dosage form so defined in claim 1 wherein the drug is tramadol hydrochloride.

3. A sustained release dosage form as defined in claim 1 wherein the diluent is lactose monohydrate.

4. A sustained release dosage form as defined in claim 1 wherein the flow control aid is colloidal silicon dioxide.

5. A sustained release dosage form as defined in claim 1 wherein the water insoluble cellulose derivative is cellulose acetate.

6. A sustained release dosage form as defined in claim 1 wherein the means for releasing the drug from the dosage form is a channeling agent in the semipermeable membrane or an osmotic passageway.

7. A sustained release dosage form as defined in claim 6 wherein the means for releasing the drug is an aperture, orifice, bore, hole, weaken area or an erodible element that erodes to form the osmotic passageway for the release of the drug from the dosage form.

8. A sustained release dosage form as defined in claim 6 wherein the means for releasing the drug is a channeling agent.

9. A sustained release dosage form as defined in claim 8 wherein the channeling agent is a mixture of water soluble material and enteric material.

10. A sustained release dosage form as defined in claim 8 wherein the channeling agent is sodium chloride, potassium chloride, sucrose, sorbitol, mannitol, polyethylene glycol, propylene glycol, hydroxypropyl cellulose, hydroxypropyl methycellulose, hydroxypropyl methycellulose phthalate, cellulose acetate phthalate, polyvinyl alcohols, methacrylic acid copolymers or mixtures thereof.

11. A sustained release dosage form as defined in claim 8 wherein the channeling agent is selected from the group consisting of sucrose, polyethylene glycol, methacrylic acid copolymers or mixtures thereof.

12. A sustained release dosage form as defined in claim 1 further comprising a water soluble seal coat that is applied to the core before the semipermeable membrane coating.

13. A sustained release dosage form as defined in claim 1 wherein the plasticizer is triacetin.

14. A sustained release dosage form as defined in claim 1 wherein the peak plasma level of the drug is obtained 4 hour after administration.

15. A sustained release pharmaceutical tablet as defined in claim 14 wherein the peak plasma level of the drug is obtained 6 to 20 hours after administration.

16. A sustained release pharmaceutical tablet as defined in claim 14 wherein the peak plasma level of the drug is obtained 10 to 18 hours after administration.

17. A sustained release dosage form as defined in claim 1 further comprising 50% or less based upon the total weight of the coating of the drug on the semipermeable membrane or mixed into the semipermeable membrane to provide an immediate release of the drug.

18. A sustained release dosage form as defined in claim 1 wherein the controlled release tablet exhibits the following dissolution profile when tested in a USP type 1 apparatus at 100 rpm in 900 ml of simulated intestinal fluid (pH 7.5 phosphate buffer) and at 37° C.:

after 2 hours 0–20% of the drug is released;

after 4 hours 5–40% of the drug is released;

after 8 hours 30–75% of the drug is released;

after 12 hours not less than 50% of the drug is released;

after 16 hours not less than 60% of the drug is released; and after 20 hours not less than 70% of the drug is released;

the immediate release tablet exhibits the following dissolution profile when tested in a USP type 1 apparatus at 100 rpm in 900 ml of simulated intestinal fluid (pH 7.5 phosphate buffer) and at 37° C.:

after 2 hours 0–100% of the drug is released; and after 4 hours not less than 50% of the drug is released; and the combination of controlled release tablet and immediate release tablet exhibits the following dissolution profile when tested in a USP type 1 apparatus at 100 rpm in 900 ml of simulated intestinal fluid (pH 7.5 phosphate buffer) and at 37° C.:

after 2 hours 0–70% of the drug is released;

after 4 hours 10–90% of the drug is released;

after 8 hours 30–95% of the drug is released;

after 12 hours not less than 50% of the drug is released;

after 16 hours not less than 60% of the drug is released; and after 20 hours not less than 70% of the drug is released.

19. A sustained release dosage form as defined in claim 19 wherein the controlled release tablet exhibits the following dissolution profile when tested in a USP type 1 apparatus at 100 rpm in 900 ml of simulated intestinal fluid (pH 7.5 phosphate buffer) and at 37° C.:

after 2 hours 0–10% of the drug is released;

after 4 hours 10–35% of the drug is released;

after 8 hours 40–70% of the drug is released;

after 12 hours not less than 60% of the drug is released;

after 16 hours not less than 70% of the drug is released; and after 20 hours not less than 80% of the drug is released;

the immediate release tablet exhibits the following dissolution profile when tested in a USP type 1 apparatus at 100 rpm in 900 ml of simulated intestinal fluid (pH 7.5 phosphate buffer) and at 37° C.:

after 2 hours 30–100% of the drug is released; and after 4 hours not less than 70% of the drug is released; and the combination of controlled release tablet and immediate release tablet exhibits the following dissolution profile when tested in a USP type 1 apparatus at 100 rpm in 900 ml of simulated intestinal fluid (pH 7.5 phosphate buffer) and at 37° C.:

after 2 hours 0–60% of the drug is released;

after 4 hours 30–80% of the drug is released;

after 8 hours 40–90% of the drug is released;

after 12 hours not less than 60% of the drug is released;

after 16 hours not less than 70% of the drug is released; and after 20 hours not less than 80% of the drug is released.

* * * * *